United States Patent
Benning (10) Patent No.: US 10,548,687 B2
(45) Date of Patent: Feb. 4, 2020

(54) SYSTEM FOR REMINDING USE OF AN ORAL CARE APPLIANCE

(71) Applicant: KONINKLIJKE PHILIPS N.V., Eindhoven (NL)

(72) Inventor: Wolter F. Benning, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 858 days.

(21) Appl. No.: 15/109,705

(22) PCT Filed: Jan. 5, 2015

(86) PCT No.: PCT/IB2015/050067
§ 371 (c)(1),
(2) Date: Jul. 5, 2016

(87) PCT Pub. No.: WO2015/101954
PCT Pub. Date: Jul. 9, 2015

(65) Prior Publication Data
US 2016/0324595 A1    Nov. 10, 2016

Related U.S. Application Data (60) Provisional application No. 61/923,801, filed on Jan. 6, 2014.

(51) Int. Cl.
*A61C 1/00* (2006.01)
*A61C 15/00* (2006.01)
(Continued)

(52) U.S. Cl.
CPC ............ *A61C 1/0015* (2013.01); *A61C 1/088* (2013.01); *A61C 15/00* (2013.01); *A61C 17/0202* (2013.01); *A61C 17/028* (2013.01)

(58) Field of Classification Search
CPC ... A61C 1/0015; A61C 1/088; A61C 17/0202; A61C 15/00; A61C 17/028;
(Continued)

(56) References Cited

U.S. PATENT DOCUMENTS 5,928,505 A * 7/1999 Inakagata .............. A61C 17/02
204/228.1
7,067,945 B2   6/2006 Grez et al.
(Continued)

FOREIGN PATENT DOCUMENTS

CN    101247769 A    8/2008
CN    201179123 Y    1/2009
(Continued)

*Primary Examiner* — Quang D Thanh (57) ABSTRACT

A flossing appliance with a body portion which includes a system for generating bursts of liquid and/or a liquid/gas mixture. A neck portion extends from the body portion through which the bursts are delivered to a nozzle, which is shaped and adapted to fit into the interproximal spaces of the user's teeth. A use reminder system which includes a reminder timer which begins to time following the activation cycle of the appliance. An indicator is responsive to the timer, providing an indication to the user that the timer has exceeded a predetermined time, such as 24 hours, without use.

15 Claims, 6 Drawing Sheets

(51) Int. Cl.
*A61C 17/00* (2006.01)
*A61C 17/02* (2006.01)
*A61C 17/028* (2006.01)
*A61C 1/08* (2006.01)

(58) Field of Classification Search
CPC .. A61C 17/221; A61H 9/0021; A61H 9/0028; A61H 13/00
USPC .......................................... 601/160, 161, 162
See application file for complete search history.

(56) References Cited

U.S. PATENT DOCUMENTS

| | | | |
|---|---|---|---|
| 8,358,203 | B1 | 1/2013 | Perry |
| 2004/0134000 | A1* | 7/2004 | Hilfinger ............ A46B 15/0002 15/22.1 |
| 2005/0211262 | A1 | 9/2005 | Raab |
| 2006/0086369 | A1 | 4/2006 | Wilkinson |
| 2008/0109973 | A1* | 5/2008 | Farrell .................... A46B 7/04 15/4 |
| 2008/0313829 | A1* | 12/2008 | Dabrowski .......... A61C 17/221 15/22.1 |
| 2010/0281636 | A1* | 11/2010 | Ortins ..................... A46B 9/04 15/4 |
| 2013/0000059 | A1 | 1/2013 | Jungnickel et al. |

FOREIGN PATENT DOCUMENTS

| | | |
|---|---|---|
| CN | 101454055 A | 6/2009 |
| CN | 102405029 A | 4/2012 |
| CN | 103153128 A | 6/2013 |
| DE | 10101163 A1 | 7/2002 |
| JP | 2008525067 A | 7/2008 |
| WO | 0178623 A1 | 10/2001 |
| WO | 2006069644 A1 | 7/2006 |
| WO | 2006125204 A2 | 11/2006 |
| WO | 2010076694 A1 | 7/2010 |
| WO | 2010129755 A1 | 11/2010 |
| WO | 2011077291 A1 | 6/2011 |
| WO | WO2012040146 A2 | 3/2012 |
| WO | 2013000059 A1 | 1/2013 |
| WO | 2013093717 A1 | 6/2013 |

\* cited by examiner

SYSTEM FOR REMINDING USE OF AN ORAL CARE APPLIANCE

CROSS-REFERENCE TO PRIOR APPLICATIONS

This application is the U.S. National Phase application under 35 U.S.C. § 371 of International Application No. PCT/IB2015/050067, filed on Jan. 5, 2015, which claims the benefit of U.S. Provisional Patent Application No. 61/923, 801, filed on Jan. 6, 2014. These applications are hereby incorporated by reference herein.

TECHNICAL FIELD

This invention relates generally to oral care appliances, particularly those appliances having a water/spray or jet for use in interproximal spaces, and more particularly concerns monitoring regular use of such an appliance.

BACKGROUND OF THE INVENTION

It is well established that proper oral care is important for general health. A first or primary routine is effective cleaning of the teeth surfaces. This can be done with various oral care appliances, although power toothbrushes have been proven to produce superior results. One such appliance is the Sonicare® toothbrush, manufactured by Philips. Such an appliance is shown in U.S. Pat. No. 7,067,945.

A secondary oral care routine is proper care/cleansing of the interproximal spaces and the gums. This is typically accomplished by flossing. However, flossing has proven to be problematic for most users. As an alternative, various appliances have been developed, including an alternative flossing device using a liquid/air spray or jet. However, it is recognized that a user can readily forget or neglect to use such an appliance due to time constraints or other concerns. Further, such devices typically do not provide any direct encouraging feedback for successful use and regular use often declines without such feedback.

Accordingly, it is desirable to provide such a flossing appliance with the capability of regularly reminding the user to use the appliance.

SUMMARY OF THE INVENTION

Accordingly, a flossing appliance for teeth comprises: an appliance body portion which includes a system for generating bursts of liquid or a liquid/gas mixture, upon activation by a user; a neck portion extending from the body portion, through which the bursts of liquid and/or liquid/gas are delivered to a nozzle which is shaped and adapted to fit into the interproximal spaces of a user's teeth; a reminder system within the body portion which includes a reminder timer which begins to time at a selected point following an activation of the appliance; and a first level indication directed to the user when the time of the reminder timer reaches or exceeds a first level reminder time.

Best Mode for Carrying Out the Invention

Figure 1:
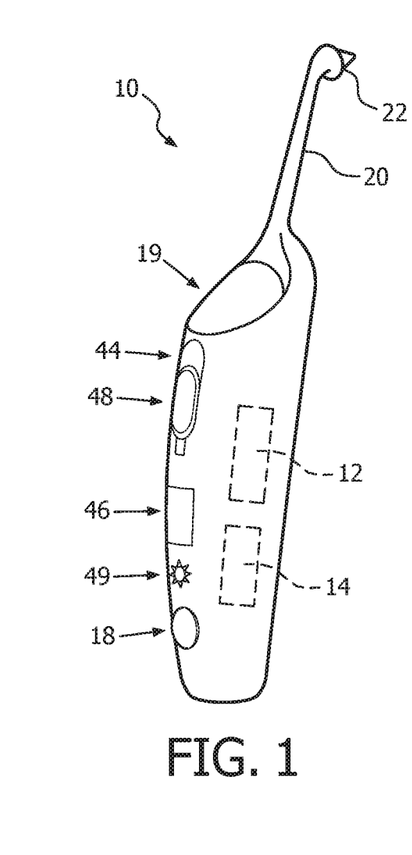
FIG. 1 is a schematic view of a liquid/air flossing appliance.

FIG. 1 is a schematic view of a liquid/air flossing appliance 10. The appliance can produce a spray, a jet or pulses, upon each activation by a user. Other types of output can also be produced. The appliance 10 includes a body portion 11, which typically includes a spray/jet generating assembly, shown generally at 12, and a power source, such as a battery 14, which can be rechargeable. Such an appliance is disclosed in more detail in U.S. patent application Ser. No. 12/344,852, the contents of which are incorporated by reference. The appliance 10 includes an ON/OFF button 18 and an activation button 19 which, when operated by the user, produces a burst of a liquid or liquid/air mixture. The liquid can be various fluids, including water, mouthwash or other liquids.

The burst of liquid/air is directed through an elongated neck portion 20 with a nozzle 22 at a distal end thereof. The nozzle has a forward shape which extends into the interproximal areas of the teeth, producing a cleansing action therebetween, as well as producing a clinically effective result on the gums. The nozzle itself is shown and disclosed in U.S. patent application Ser. No. 13/512,059, the contents of which are hereby incorporated by reference. Various nozzle configurations, however, can be used, as long as they fit into the interproximal spaces.

The present invention is directed toward a system for reminding the user to regularly use appliance 10. In the embodiment shown, it is recognized that one use per day is effective, and the reminder is based on a 24-hour cycle, although other reminder cycles can be used.

Figure 2:
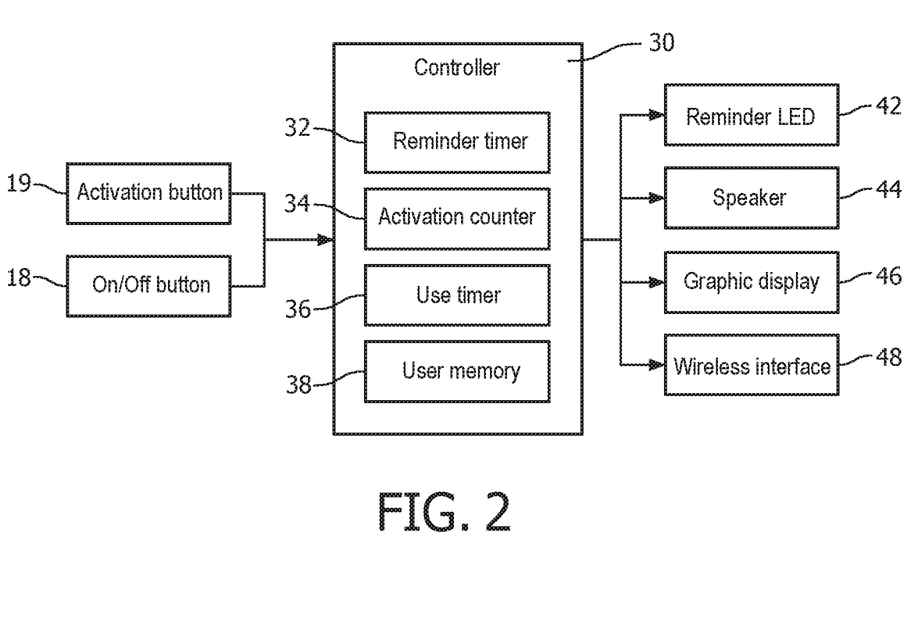
FIG. 2 is a block diagram of the system for reminding users to use the appliance.

FIG. 2 shows a basic block diagram of the operating structure of the appliance with the reminder system. FIGS. 3-6 show software control flow charts for the various embodiments of the reminder system. FIG. 2 includes the ON/OFF button 18 and the activation button 19, as discussed above for the appliance 10. The ON/OFF button and the activation button interface with a controller system, shown generally at 30, which includes a reminder timer 32, an activation counter 34, a use timer 36 and a use memory 38. The counter 34, timer 36 and memory 38 are used in optional, different embodiments. Controller 30 operates one or more of a reminder LED 42, a speaker 44, a graphic display 46 and a wireless interface 48.

Figure 3:
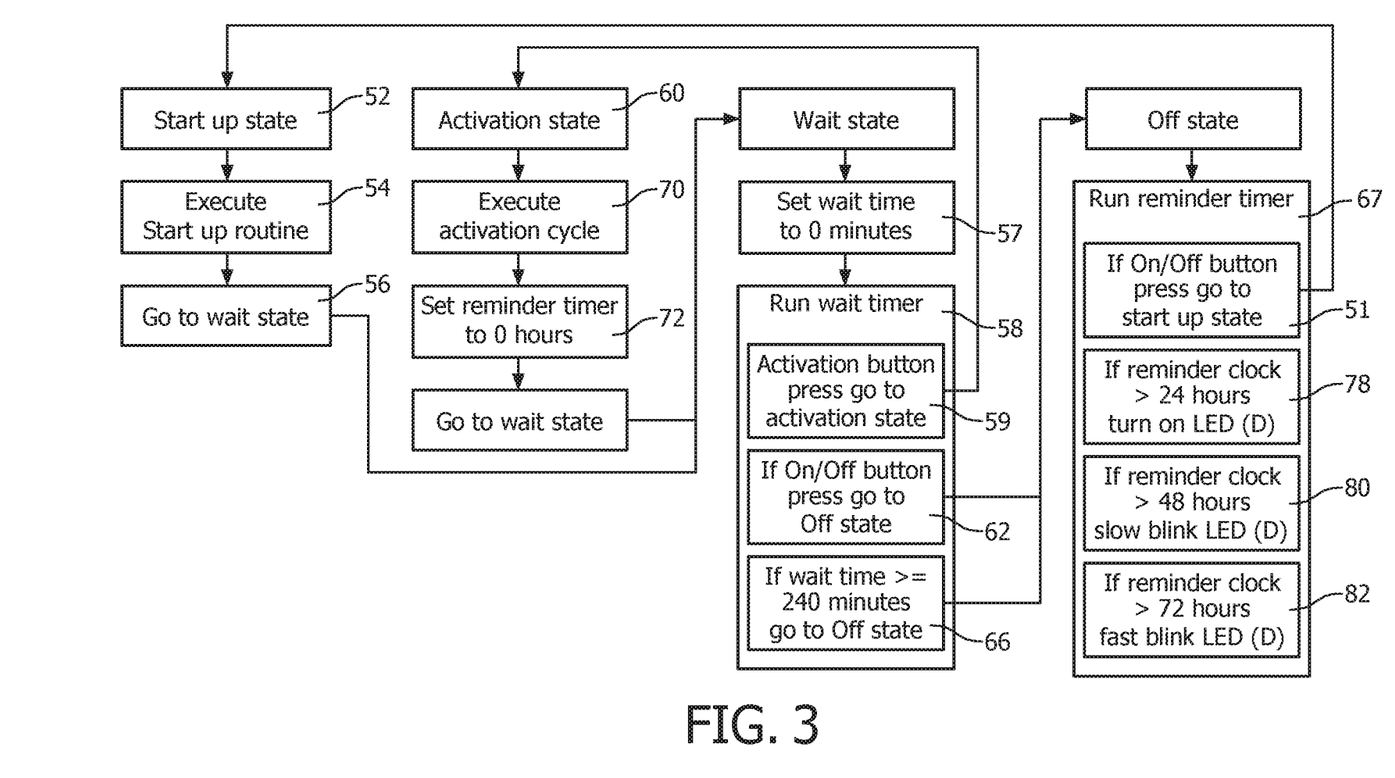
FIG. 3 is a basic control flow chart for operation of the reminder system.

FIG. 3 shows the basic software control flow chart. If ON/OFF button 18 is pressed to an ON condition from an off condition, as represented at 51, the software goes to a start-up state, as represented at 52. The software then executes a start-up routine, at 54. The start-up routine then proceeds to a wait state or condition, at 56. The wait time is set to zero minutes at 57, and a wait timer 58 begins to time. When the activation button 19 is pressed by the user, the software proceeds to the activation state, at 60. If the ON/OFF button is pressed from ON to OFF, at 62, or if the wait time extends for 240 minutes, or another selected time, the software proceeds to the OFF state, at 66, and the reminder timer 32 begins to time, at 67.

Alternatively, when the activation button 19 is pressed when the appliance is in an ON condition, the program executes the activation cycle, at 70, the reminder timer 32 is set to zero hours, at 72, and the software proceeds to the wait state, as described above. In normal use, following the "wait time" in 66, the reminder timer will start to run. A first level reminder time is set for 24 hours, for the embodiment shown, at 78. Other first level reminder times could be used. In the embodiment shown, a first level indication is a visual indicator, such as a lit LED 49 (FIG. 1), of a selected color, such as red. If the reminder clock exceeds 48 hours (second level reminder time) in the embodiment shown, a second level reminder occurs, shown at 80, which in the embodiment shown is a slow blinking LED, such as a rate of ½-1 Hz. If the reminder clock exceeds 72 hours (a third level reminder time) without the reminder timer being reset by a use, a third level reminder/indication occurs, which in the embodiment shown is a fast blinking LED, such as a rate of 2-4 Hz.

The first level reminder is to provide a non-annoying indication to the user. The second level reminder is intended to provide a more intense indication to the user, attempting to obtain the user's attention in a stronger fashion, while the third level reminder is intended to be of sufficiently high intensity to provoke action on the part of the user. It should be understood that other forms of indications to the user, different than visual (e.g. LED) can be used. Further, it should be understood that the first level reminder comprises the basic embodiment, while the second and third level reminders comprise more detailed embodiments.

Figure 4:
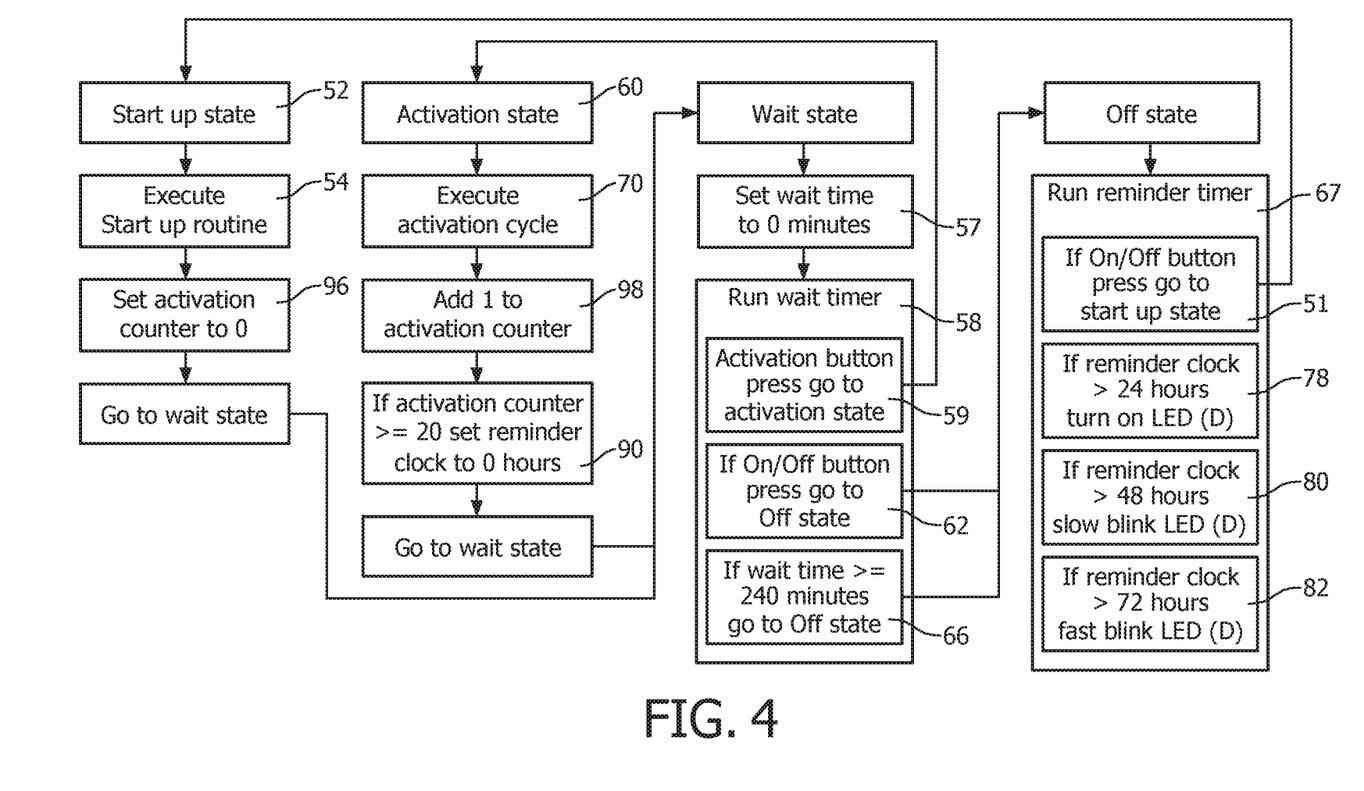
FIG. 4 is a modified control flow chart, including an activation counter system.

FIG. 4 is a software flow chart, similar to FIG. 3, with additional software control steps. Following the execution of the start-up routine at 52, an activation counter is set to zero, as shown at 86 and an activation counter 88 is incremented by one. When the activation counter equals or is greater than 20, in the embodiment shown, or other preselected number, as shown at 90, the reminder clock is set to zero. The activation counter is used to ensure that there has been an actual reasonably complete use cycle of the device before the reminder time is reset to zero.

Figure 5:
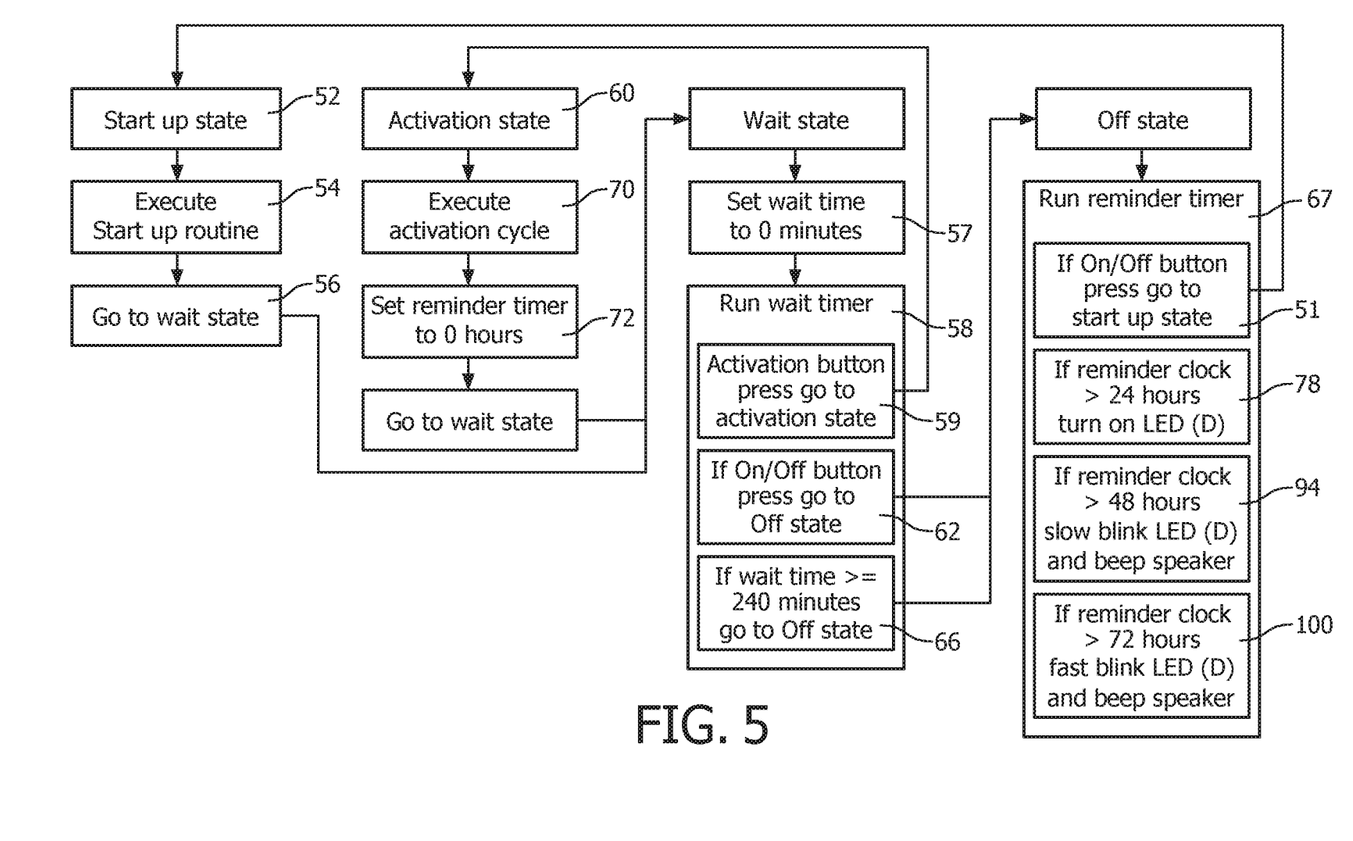
FIG. 5 is a modified control flow chart, including an audible indication capability.

FIG. 5 shows a modification of the basic flow chart of FIG. 3, with the addition of an audible indication, by virtue of a speaker 44 on the appliance body. In this embodiment, at a level one reminder, an LED is turned on at 24 hours after the last use. For a second level reminder, at 48 hours, the LED has a slow blink rate, with a second level sound indication, particularly a beep sound from the speaker 48, shown at 94. If the reminder clock exceeds 72 hours, the LED will fast blink and the sound from the speaker will increase in volume (louder), or be a harsher (jarring), more intense sound, as shown at 100.

Figure 6:
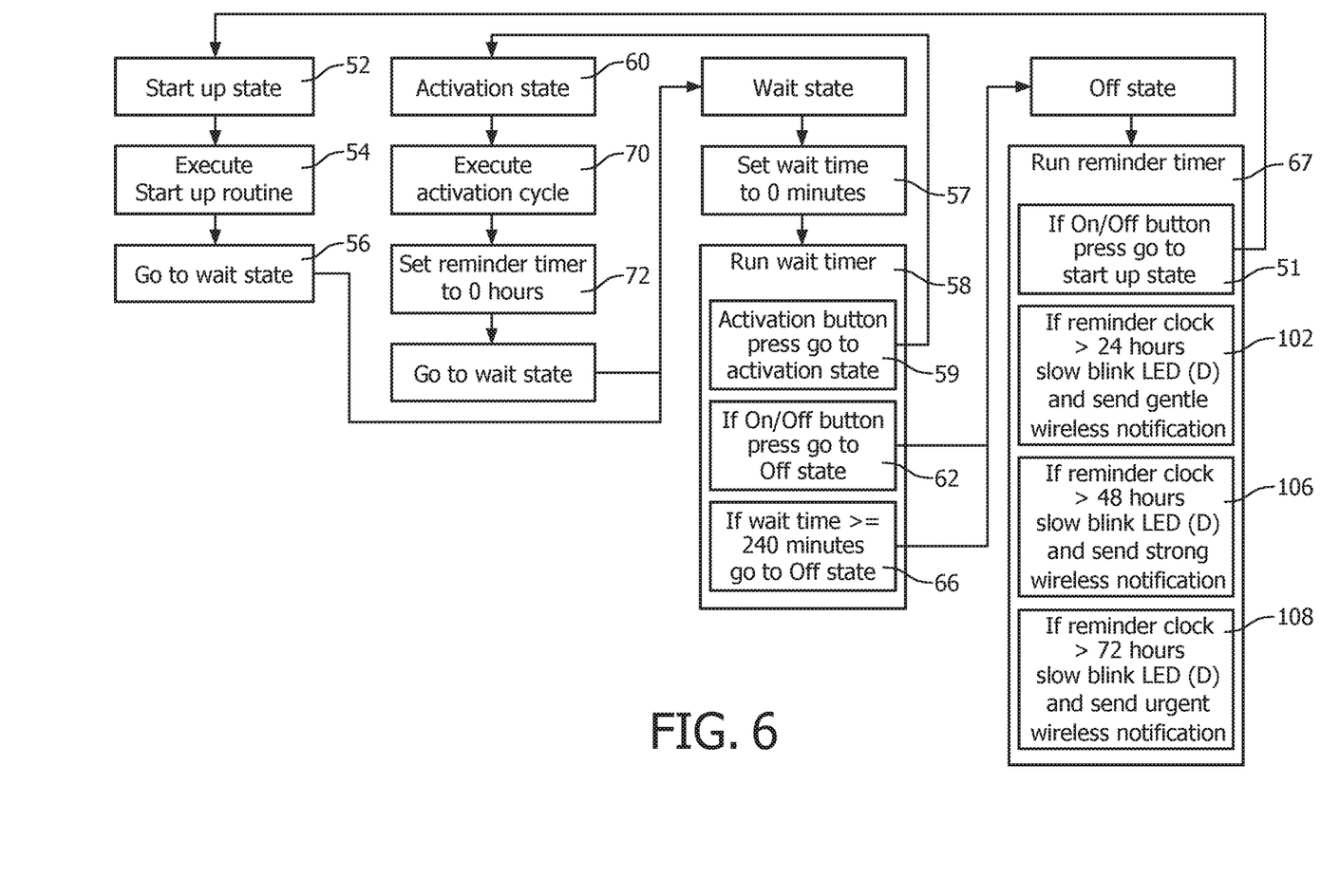
FIG. 6 is a modified control flow chart which includes a wireless notification capability.

FIG. 6 shows another embodiment of the software control of FIG. 3, but including a wireless notification which can be sent to an external device, such as a mobile device, including a phone, a tablet or computer. This can be done by various wireless connections, such as WiFi, Bluetooth, etc. In this embodiment, for a first reminder (first predetermined time) at 24 hours, there will be a slow blinking LED and a first wireless notification, a gentle notification, represented at 102. A second reminder (second predetermined time) at 48 hours is a slow blinking LED and a second wireless notification, a strong wireless notification, as represented at 106. The third level reminder, at 72 hours, includes a slow blinking LED and an urgent wireless notification, as represented at 108.

Figure 7:
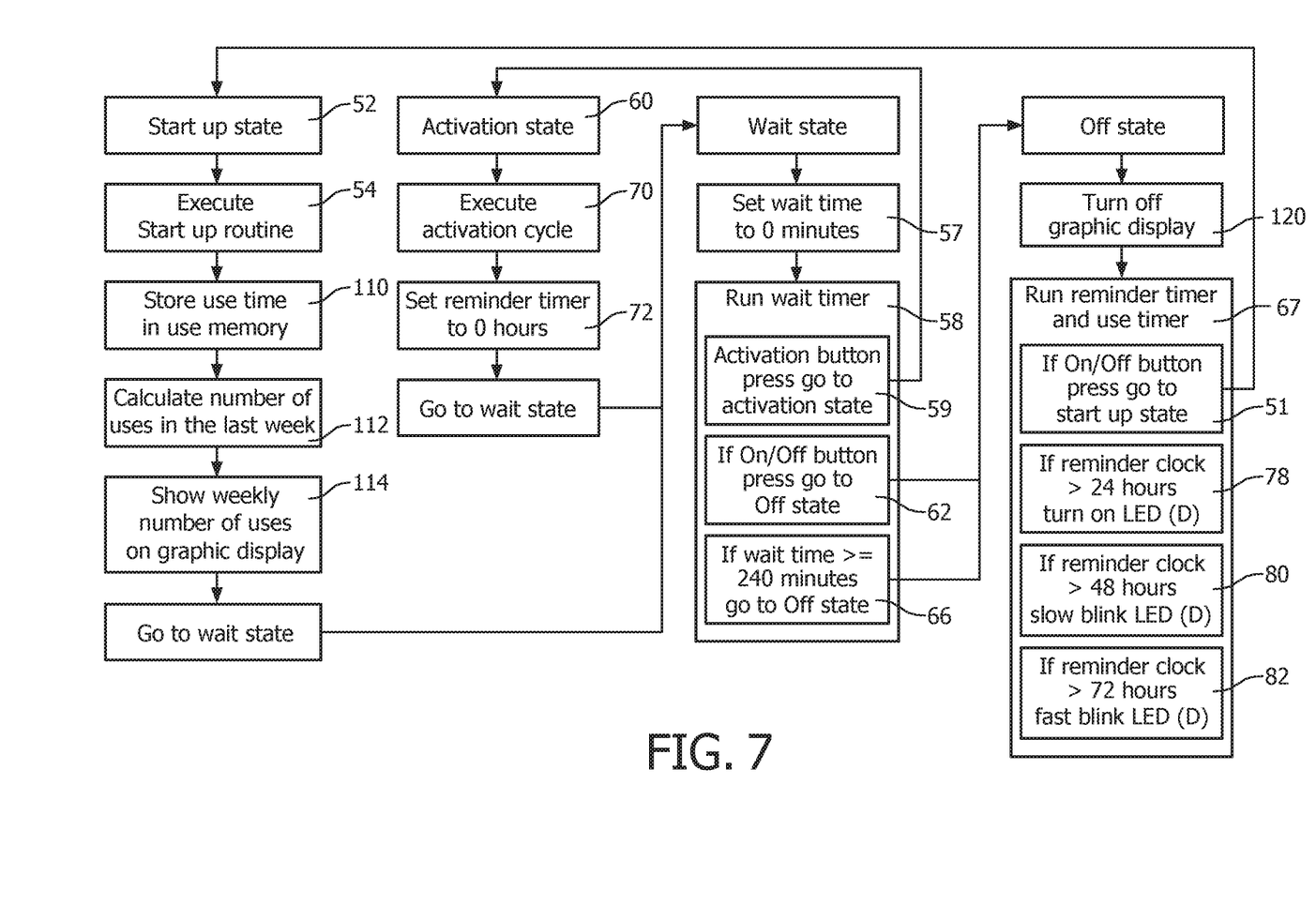
FIG. 7 is a modified control flow chart, wherein the appliance includes a graphical display.

FIG. 7 shows a software control flow chart similar to that of FIG. 3, with the control of graphical display 46 in the appliance. In the flow chart, following the execution of the start-up routine at 54, the actual use time is stored in a use memory, as represented at 110. The number of uses in the past week will then be calculated, shown at 112, and the actual number of uses will be shown on the graphic display, as shown at 114. Other display periods could be used, two weeks, for instance, when the appliance is in an OFF state, regardless of the cause. The graphic display will turn off at 120.

Accordingly, a reminder system for use of a power flossing appliance has been disclosed. It includes a first level reminder at 24 hours, for a once-a-day reminder, with various indications, including in one embodiment the use of an LED. Other indications, including audible or wireless, can be used. Additional reminder levels can be provided, including a second level, typically after 48 hours, and a third level, typically 72 hours, which provide stronger reminders. The second and third level reminders can be provided by varying the initial reminder indication in some manner, or by adding additional indications, such as combining indications in some way to increase the level of attention to the user.

Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:

1. A flossing appliance for teeth, comprising:
   an appliance body portion which includes a system for generating bursts of liquid or a liquid/gas mixture, upon activation by a user;
   a neck portion extending from the body portion, through which the bursts of liquid and/or liquid/gas mixture are delivered to a nozzle which is shaped and adapted to fit into the interproximal spaces of a user's teeth;
   a reminder system within the body portion which includes a reminder timer which begins to time at a selected time following an activation of the system for generating bursts of liquid or a liquid/gas mixture, wherein the selected time is determined via an activation counter used to ensure an actual complete use cycle of the flossing appliance before the reminder timer is reset to zero; and
   a first level indication directed to the user when the selected time of the reminder timer reaches or exceeds a first level reminder time.

2. The flossing appliance of claim 1, wherein the first level reminder time is 24 hours.

3. The flossing appliance of claim 1, wherein the first level indication comprises one selected from the group consisting of a first visual indicator, a first audible indication, and a first wireless notification sent to an external device.

4. The flossing appliance of claim 3, wherein the first level indication comprises the first visual indicator that is a Light-Emitting Diode (LED).

5. The flossing appliance of claim 3 wherein the external device comprises a mobile device.

6. The flossing appliance of claim 3, further comprising a second level indication directed to the user at a second level reminder time when a second level reminder time is reached or exceeded, wherein the second level reminder time is longer than the first level reminder time.

7. The flossing appliance of claim 6, wherein the second level reminder time is 48 hours.

8. The flossing appliance of claim 6, wherein the second level indication at the second level reminder time comprises at least one selected from the group consisting of a blinking Light-Emitting Diode (LED) at a first blinking rate, an audible indication to accompany the blinking LED at the first blinking rate, and a second wireless notification.

9. The flossing appliance of claim 8, further comprising a third level indication directed to the user when a third level reminder time is reached or exceeded, wherein the third level reminder time is longer than the second level reminder time.

10. The flossing appliance of claim 9, wherein the third level reminder time is 72 hours.

11. The flossing appliance of claim 9, wherein the third level indication is at the third level reminder time comprises at least one selected from the group consisting of (i) a blinking Light-Emitting Diode (LED) at a rate faster than the first blinking rate of the second level reminder time, (ii) an audible sound that comprises at least one of being louder and harsher than the audible indication of the second level indication, and (iii) the blinking LED at the rate faster than the first blinking rate of the second level indication and a third wireless notification having a message marked urgent sent to an external device.

12. The flossing appliance of claim 1, wherein the reminder system comprises a controller and a memory for calculating a number of uses of the flossing appliance in a selected period and for displaying said uses on a display in the appliance body portion of the flossing appliance.

13. The flossing appliance of claim 12, wherein the selected period is one week.

14. The flossing appliance of claim 1, further comprising a wait timer which begins to time following the user pressing an ON/OFF button, wherein when the system for generating bursts of liquid or a liquid/gas mixture is not activated within a predetermined time, the flossing appliance proceeds to an off state.

15. The flossing appliance of claim 1, wherein subsequent to execution of a start-up routine in response to the flossing appliance transitioning, via an ON/OFF button, to an ON condition from an OFF condition, the activation counter accumulates a number of activations in which the system for generating bursts of liquid or a liquid/gas mixture has been activated while the flossing appliance is in the ON condition, the activation counter incrementing by one in response to each activation, and further wherein, responsive to the activation counter reaching a count that is greater than or equal to a preselected number of activations, the reminder timer resets to zero.

* * * * *